United States Patent
Fogelberg et al.

(10) Patent No.: US 10,004,625 B2
(45) Date of Patent: Jun. 26, 2018

(54) EATING AID ROBOT AND METHOD FOR CONTROLLING THE SAME

(71) Applicant: BESTIC AB, Stockholm (SE)

(72) Inventors: Jonathan Fogelberg, Stockholm (SE); Ann-Louise Lindborg, Enskede (SE)

(73) Assignee: Bestic AB, Nacka (SE)

( * ) Notice: Subject to any disclaimer, the term of this patent is extended or adjusted under 35 U.S.C. 154(b) by 68 days.

(21) Appl. No.: 15/093,849

(22) Filed: Apr. 8, 2016

(65) Prior Publication Data
US 2016/0220404 A1    Aug. 4, 2016

Related U.S. Application Data

(63) Continuation of application No. PCT/SE2014/051192, filed on Oct. 9, 2014.

(30) Foreign Application Priority Data

Oct. 9, 2013   (SE) ...................................... 1351189

(51) Int. Cl.
G06F 19/00       (2018.01)
A61F 4/00        (2006.01)
B25J 11/00       (2006.01)
B25J 9/16        (2006.01)

(52) U.S. Cl.
CPC .............. *A61F 4/00* (2013.01); *B25J 9/1679* (2013.01); *B25J 11/008* (2013.01); *B25J 11/009* (2013.01); *G05B 2219/45111* (2013.01)

(58) Field of Classification Search
CPC ......... A61F 4/00; B25J 9/1679; B25J 11/008; B25J 11/009
See application file for complete search history.

(56) References Cited

U.S. PATENT DOCUMENTS

| | | | | |
|---|---|---|---|---|
| 5,037,261 A | * | 8/1991 | Morewood | A47G 21/08 414/4 |
| 5,282,711 A | * | 2/1994 | Frische | A47G 19/02 414/744.4 |
| 6,592,315 B2 | | 7/2003 | Osborne | |
| 8,240,967 B2 | * | 8/2012 | Guglielmelli | A47G 21/08 414/9 |

(Continued)

FOREIGN PATENT DOCUMENTS

EP    0523292 A1    1/1993

*Primary Examiner* — Mingjen Jen
(74) *Attorney, Agent, or Firm* — Gabriela B. Tomescu, Esq.; Bergenstråhle & Partners AB

(57) ABSTRACT

An eating aid robot and a method performed thereby are provided. The robot comprises an arm capable of engaging an eating tool at an end of the arm. The arm is moveable to move the eating tool horizontally and vertically, wherein the arm is configured to be positioned with the eating tool in at least two vertical levels. The robot is connectable to a maneuver device which sends a signal to the robot, wherein the arm follows a cycle of different vertical and horizontal movements and pauses when the arm is kept still with the eating tool in at least one of the vertical levels. The method comprises receiving the signal from the maneuver device, and selecting a subsequent movement and/or pause of the cycle for the arm based on in which of the movements or pauses of the cycle the arm currently is when receiving the signal.

19 Claims, 11 Drawing Sheets

(56) References Cited

U.S. PATENT DOCUMENTS

| | | | | |
|---|---|---|---|---|
| D740,071 S | * | 10/2015 | Dekar | D7/505 |
| 9,504,343 B2 | * | 11/2016 | Dekar | A47G 21/08 |
| 2002/0064438 A1 | * | 5/2002 | Osborne, Jr. | A47G 21/08 414/9 |
| 2007/0217891 A1 | * | 9/2007 | Folcik | A47G 21/08 414/9 |
| 2013/0041506 A1 | | 2/2013 | Dekar | |
| 2013/0090756 A1 | * | 4/2013 | Dekar | A47G 21/08 700/213 |
| 2013/0203024 A1 | | 8/2013 | Dekar | |

\* cited by examiner

US 10,004,625 B2

EATING AID ROBOT AND METHOD FOR CONTROLLING THE SAME

This application is the continuation of international Application No. PCT/SE2014/051192, filed on 9 Oct. 2014 which claims the benefit of Swedish patent application SE 1351189-4, filed 9 Oct. 2013, the entire contents of which are hereby incorporated by reference.

TECHNICAL FIELD

The present disclosure relates to eating aid arrangements and in particular to eating aid robots and method performed thereby.

BACKGROUND

A person may suffer from a handicap which makes it difficult for that person to be able to eat by himself/herself. There are many different handicaps that may render a person having difficulties eating himself/herself.

If a person in not able to eat by himself/herself, he/she needs help to be fed, for example by having an assisting person feeding him/her. However, being fed may be experienced as degrading and/or uncomfortable. Thus it is preferable if the handicapped person is enabled to help himself/herself.

Different eating aid robots have been proposed in order to help persons with disabilities to feed themselves. However, due to the type of disability the person is suffering from, it may be very difficult for some users to control the eating aid robot to help the user with eating.

SUMMARY

The object is to obviate at least some of the problems outlined above. In particular, it is an object to provide an eating robot and a method performed by the eating robot for controlling the eating robot. These objects and others may be obtained by providing an eating robot and a method performed by the eating robot according to the independent claims attached below.

According to an aspect a method for controlling an eating robot is provided. The eating aid robot comprises an arm capable of engaging an eating tool at an end of the arm. The arm is moveable to move the eating tool horizontally and vertically, wherein the arm of the eating aid robot is configured to be positioned with the eating tool in at least two vertical levels, a first vertical level and a second vertical level at a vertical height above the first vertical level. The eating aid robot is connectable to a manoeuvre device which sends a signal to the robot at various time instances during operation of the eating aid robot, wherein the arm of the eating robot further follows a cycle of different vertical and horizontal movements and pauses when the arm is kept still with the eating tool in at least one of the vertical levels. The method comprises receiving the signal from the manoeuvre device, and selecting a subsequent movement and/or pause of the cycle for the arm based on in which of the movements or pauses of the cycle the arm currently is when receiving the signal. The method further comprises executing the selected subsequent movement and/or pause of the cycle until the signal is received anew from the manoeuvre device.

According to an aspect, an eating aid robot is provided. eating aid robot comprises an arm capable of engaging an eating tool at an end of the arm. The arm is moveable to move the eating tool horizontally and vertically, wherein the arm of the eating aid robot is configured to be positioned with the eating tool in at least two vertical levels, a first vertical level and a second vertical level at a vertical height above the first vertical level. The eating aid robot is connectable to a manoeuvre device which sends a signal to the robot at various time instances during operation of the eating aid robot, wherein the arm of the eating robot further follows a cycle of different vertical and horizontal movements and pauses when the arm is kept still with the eating tool in at least one of the vertical levels. The eating aid robot comprises a receiving unit adapted for receiving the signal from the manoeuvre device; and a selecting unit adapted for selecting a subsequent movement and/or pause of the cycle for the arm based on in which of the movements or pauses of the cycle the arm currently is when receiving the signal. The eating aid robot further comprises an executing unit adapted for executing the selected subsequent movement and/or pause of the cycle until the signal is received anew from the manoeuvre device.

Both the eating aid robot and the method performed by the eating aid robot may have several advantages. For a person who may have difficulty manoeuvring e.g. a joystick in different directions, or pressing a plurality of different buttons, in order to control the arm and thus the eating tool, a simple button is enough to control the movements of the arm and thus the eating tool, or pressing any button out of a plurality of buttons, moving a joystick in any of a plurality of directions is enough to control the movements of the arm and thus the eating tool. A person having difficulties eating himself/herself may experience enhanced eating quality by an easily controllable eating aid robot.

BRIEF DESCRIPTION OF DRAWINGS

Embodiments will now be described in more detail in relation to the accompanying drawings, in which.

DETAILED DESCRIPTION

Briefly described, an eating robot and a method for controlling the eating robot are provided. The eating robot is connectable to a manoeuvre device which sends a signal to the robot at various time instances during operation of the eating aid robot.

Embodiments of a method for controlling the eating robot will now be described with reference to FIGS. 1a-1d.

Figure 1A:
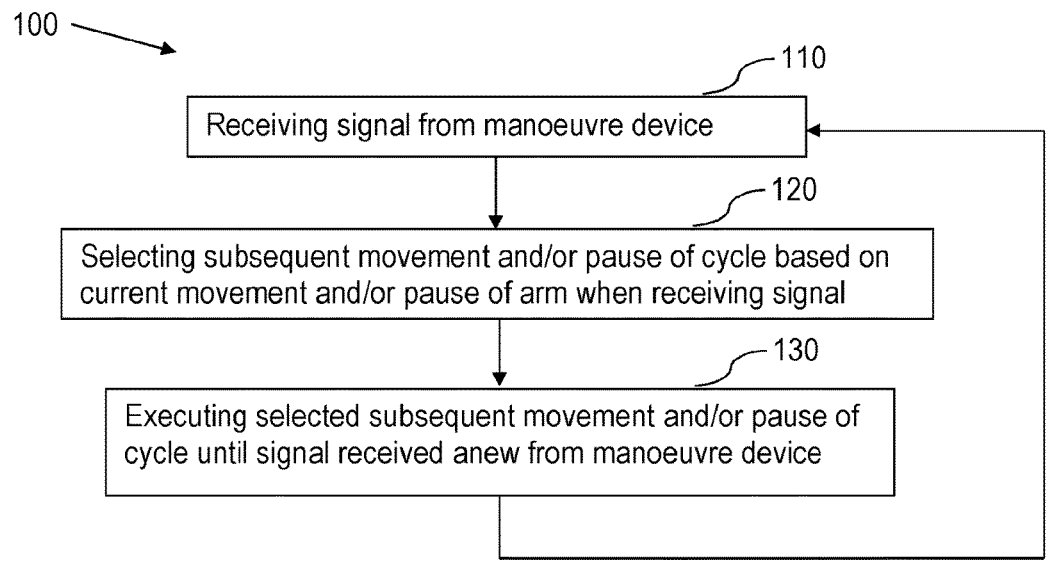
FIG. 1a is a flowchart of a method for controlling an eating aid robot according to an exemplifying embodiment.
Figure 1B:
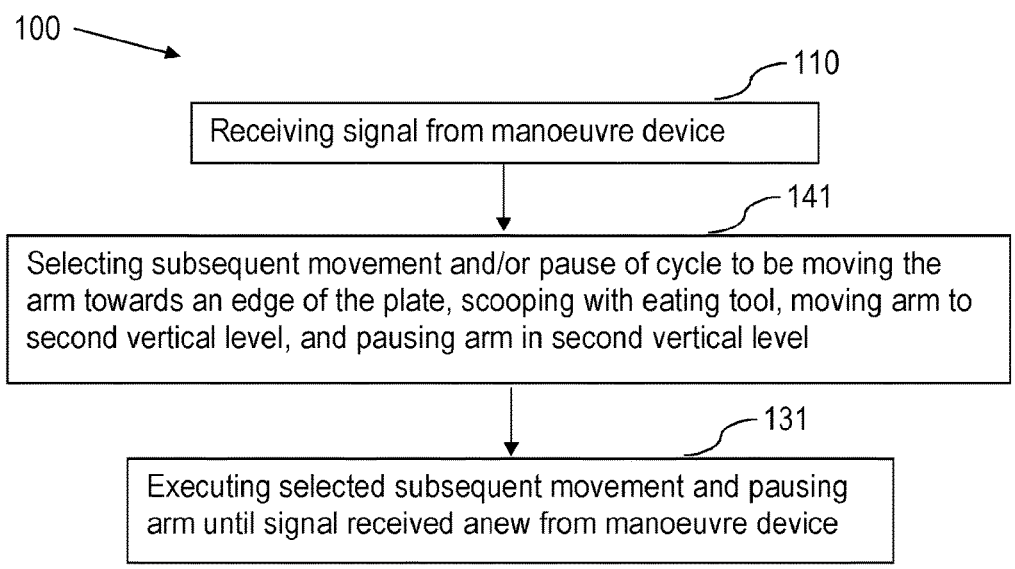
FIG. 1b is a flowchart of a method for controlling an eating aid robot according to still an exemplifying embodiment.

The eating aid robot comprises an arm capable of engaging an eating tool at an end of the arm. The arm is moveable to move the eating tool horizontally and vertically, wherein the arm of the eating aid robot is configured to be positioned with the eating tool in at least two vertical levels, a first vertical level and a second vertical level at a vertical height above the first vertical level. The eating aid robot is connectable to a manoeuvre device which sends a signal to the robot at various time instances during operation of the eating aid robot, wherein the arm of the eating robot further follows a cycle of different vertical and horizontal movements and pauses when the arm is kept still with the eating tool in at least one of the vertical levels. FIG. 1a illustrates the method comprising receiving 110 the signal from the manoeuvre device, and selecting 120 a subsequent movement and/or pause of the cycle for the arm based on in which of the movements or pauses of the cycle the arm currently is when receiving the signal. The method further comprises executing 130 the selected subsequent movement and/or pause of the cycle until a signal is received anew from the manoeuvre device.

The eating aid robot is to be used by a person for helping him/her to eat. The eating aid robot may be placed on a table upon which also a dinner plate or any other type of container, e.g. bowl or bento box, on or in which food may be placed. Hereinafter, the term plate will be used and it is to be understood that the plate may be any other type of container in which food may be placed. The eating aid robot may alternatively be placed on (or mounted to) a rack, stand, frame, platform or the like, which may stand on a floor. The eating aid robot comprises an arm with is capable of engaging an eating tool at an end of the arm. The eating tool may be e.g. a spoon, a fork, chopsticks, a gripping device or any other sort of tool which may be used for picking up food from e.g. a dinner plate. Depending on the kind of food that is, the handicap of the person using the eating aid robot or on the culture in which the eating aid robot is used, different eating tools may be preferable to use. For example, if the food to be eaten is soup, then the eating tool may be a spoon. If the eating aid robot is used in a culture where chopsticks are used, then the eating tool may be chopsticks or a gripping device. Still as an example, if the person using the eating aid robot suffers from Parkinson's disease or any other condition (e.g. Cerebral Pares) so that the person using the eating aid robot have problems controlling his/her movements, then a fork may be unsuitable irrespective of the food to be eaten by the person and then a spoon may be preferable.

The arm is moveable to move the eating tool horizontally and vertically, wherein the arm of the eating aid robot is configured to be positioned with the eating tool in at least two vertical levels, a first vertical level and a second vertical level at a vertical height above the first vertical level. The first vertical level may be at or directly above the plate holding the food and the second vertical level is at a vertical height above the first vertical level, e.g. about the vertical level of the mouth of a person using the eating aid robot. It shall be pointed out that the arm of the eating aid robot is configured to be positioned with the eating tool in more than two vertical positions, e.g. three, where one vertical position is at the plate, another e.g. few centimeters above the plate and the last one at a vertical level about the vertical level of the mouth of a person using the eating aid robot. The arm is thus moveable vertically between the different vertical levels.

The eating aid robot is connectable to a manoeuvre device which sends a signal to the robot at various time instances during operation of the eating aid robot. The manoeuvre device may be connected to the eating aid robot by wire or wirelessly. The manoeuvre device may comprise just a button or a rod/stick which may be pressed or moved in different directions respectively, wherein when the button is pressed or the rod/stick is moved in any direction, the manoeuvre device generates the same signal which is sent to the eating aid robot, irrespective of the movement of the rod/stick. These are merely examples of a manoeuvre device, other examples are angle sensors, photo sensors, suction sensors and blowing sensors. Irrespective of the type of manoeuvre device, when the manoeuvre device is "activated", it sends the one signal to the eating aid robot.

Alternatively, the manoeuvre device is connected to the eating aid robot by means of a signal converter, which converts different signals of the manoeuvre device to one type of signal.

Still alternatively, the eating aid robot interprets the received signal just as a received signal, irrespective of the type of signal. Assume for example that the manoeuvre device is a joystick sending a plurality of different signals to the eating aid robot as the stick of the joystick is moved around. For the eating aid robot, no matter what signal is received from the manoeuvre device (the joystick in this example), the eating aid robot performs the same action, i.e. selects 120 a subsequent movement and/or pause of the cycle for the arm based on in which of the movements or pauses of the cycle the arm currently is when receiving the signal and executes 130 the selected subsequent movement and/or pause of the cycle until the, or a, signal is received anew from the manoeuvre device.

The arm of the eating robot further follows a cycle of different vertical and horizontal movements, and pauses when the arm is kept still with the eating tool in at least one of the vertical levels. In other words, the eating tool may e.g. be held or kept still both vertically and horizontally during a pause of the cycle. The eating tool may further be kept still in a vertical level while being moved horizontally during a movement of the cycle. Still further, the eating tool may be moved both vertically and the horizontally during a movement of the cycle. The cycle may thus comprise a plurality of individual movements and pauses, which follow one after the other. A first movement may be followed by a second movement without a pause in between. The cycle may be pre-programmed into a memory comprised in the eating aid robot, which will be explained in more detail below. Further, the memory may comprise different cycles for different food such that the person using the eating aid robot (i.e. the user) may select what kind of food that is to be eaten, e.g. soup or bits of food. Still further, the cycles may be different so that the user may select which tool is used with the eating aid robot, and also select a cycle depending on the handicap of the user. The user may have more or less difficult of eating himself/herself and also have more or less difficulties using the manoeuvre device and different cycles may be adapted with such considerations in mind.

The method comprising receiving 110 the signal from the manoeuvre device, and selecting 120 a subsequent movement and/or pause of the cycle for the arm based on in which of the movements or pauses of the cycle the arm currently is when receiving the signal.

Merely as an example, if the arm is paused with the spoon in the second vertical level (e.g. at about the same vertical level as the mouth of the person using the robot), the user may press the button when he/she wishes to continue eating. In an example, when the signal is received 110 from the manoeuvre device and the arm is paused with the spoon in the second vertical level, the eating aid robot selects 120 the subsequent movement and/or pause of the arm to be moving the eating tool down to the first vertical level and obtaining food with the eating tool and then move the eating tool up again to the second vertical position and then pausing the arm with the eating tool in the second vertical position. It shall be pointed out that this is merely an illustrative example and the different movements and pauses of the cycle will be explained in more detail below. Also how to obtain the food with the eating tool will also be explained in more detail below. Another illustrative example is when the signal is received 110 from the manoeuvre device and the arm is paused with the spoon in the first vertical level. The eating aid robot selects 120 the subsequent movement and/or pause of the arm to be moving the eating tool horizontally in the first vertical level and obtaining food with the eating tool and then move the eating tool up to the second vertical position and then pausing the arm with the eating tool in the second vertical position.

The eating aid robot then executes 130 the selected subsequent movement and/or pause of the cycle for the arm until the signal is received anew from the manoeuvre device.

The method may have several advantages. For a person who may have difficulty manoeuvring e.g. a joystick in different directions, or pressing a plurality of different buttons, in order to control the arm and thus the eating tool, a simple button is enough to control the movements of the arm and thus the eating tool, or pressing any button out of a plurality of buttons, moving a joystick in any of a plurality of directions is enough to control the movements of the arm and thus the eating tool. A person having difficulties eating himself/herself may experience enhanced eating quality by an easily controllable eating aid robot.

The eating aid robot may be calibrated to a plate with regard to a vertical level of the plate, or the eating aid robot may comprise sensing means adapted to detect when the eating tool is pressing against a surface of the plate, wherein the first vertical level corresponds to the vertical level of the plate.

As described above, the plate may be a dinner plate or any other type of container, e.g. bowl or bento box, on or in which food may be placed. The eating aid robot may be calibrated with the plate such that the first vertical level corresponds to the vertical level of the plate. The calibration may be pre-programmed or be performed e.g. when the eating aid robot is switched on. The eating aid robot may be placed on a table together with the plate, wherein pre-programming of the vertical level of the plate is simple and independent on e.g. the height of the table.

The eating aid robot may alternatively be placed on (or mounted to) a rack, stand, frame, platform or the like. In such a case, the vertical height of tables on which plates may be placed may vary as the eating aid robot is moved from a first table to a second table. The eating aid robot may comprise sensing means adapted to detect when the eating tool is pressing against a surface of the plate. When the eating aid robot is switched in, the eating aid robot may then first find the first vertical level corresponding to the vertical level of the plate by lowering the eating tool downwards until it hits the plate, wherein the sensing means detects that the eating tool may not be lowered any further and the eating aid robot thus determines that this is the vertical level of the plate and this is the first vertical level of the eating tool.

The eating aid robot may further be calibrated to the plate with regard to the shape of the plate, or comprises sensing means adapted to detect when the eating tool is pressing against an edge of the plate, the method comprising, when the arm is positioned with the eating tool in the first vertical level corresponding to a vertical level of the plate, moving the arm to move the eating tool horizontally within the plate according to a random pattern.

In an example, the eating aid robot is always used together with at least one "known" plate. This means that the eating aid robot may be pre-programmed, or calibrated, with regards to at least one known plate. Thus, a person using the eating aid robot may give an input to the eating aid robot as to which plate is to be used. By a "known" plate is meant that the shape and size of the plate may be pre-programmed into a memory comprised in the eating aid robot. By size and shape is means e.g. circular, oval, square etc. and the respective size of the circular, oval, square etc., e.g. the diameter of the circle or the length of the edges of the square.

In another example, a plate not "known" to the eating aid robot is used, wherein the eating aid robot does not have information about the shape and size about the plate. If so, then the eating aid robot may comprise sensing means adapted for detecting when the eating tool is pressing against an edge of the plate. Thus the eating aid robot is enabled to either calibrate itself by collecting information regarding horizontal coordinates each time the sensing means detects that the eating tool is pressing against an edge of the plate, or alternatively to just stop a movement when detecting that the eating tool is pressing against an edge of the plate and optionally change movement upon such detection. By optionally changing movement is meant e.g. to stop the horizontal movement and perform another movement of the cycle, or to change the horizontal movement to another horizontal movement. The horizontal movement may be performed according to a random pattern either according to the calibration of the eating aid robot to the plate or according to the sensing means detecting that the eating tool is pressing against an edge of the plate.

The eating aid robot may further be calibrated to the plate with regard to the shape of the plate, or comprises sensing means adapted to detect when the eating tool is pressing against an edge of the plate, the method comprising, when the arm is positioned with the eating tool in the first vertical level corresponding to a vertical level of the plate, moving the arm to move the eating tool horizontally within the plate according to a predetermined pattern.

As described above, the eating aid robot may either be calibrated to the plate or comprises sensing means adapted to detect when the eating tool is pressing against an edge of the plate. Instead of the eating aid robot moving the arm to move the eating tool horizontally within the plate according to a random pattern, the eating aid robot moves the arm to move the eating tool horizontally within the plate according to the predetermined pattern.

The method may further comprise receiving 110 the signal from the manoeuvre device when the arm is currently holding the eating tool in the first vertical level and moving the eating tool within the plate, selecting 121 and executing 131 the subsequent movement and/or pause of the cycle for the arm to be moving the eating tool towards an edge of the plate based on the calibration of the eating aid robot with the shape of the plate or the sensing means detecting the eating tool pressing against the edge of the plate, scooping with the eating tool, moving the eating tool to the second vertical level and pausing the arm with the eating tool in the second vertical level until receiving 110 the signal anew from the manoeuvre device.

In this example, the arm of the eating aid robot is holding the eating tool in the first vertical level. The first vertical level corresponds to the vertical level of the plate. The arm of the eating aid robot is further moving the eating tool within the plate, i.e. on the surface of the plate within the edge(s) of the plate. As described above, the eating aid robot may be calibrated to the plate so that the eating aid robot knows the boundaries of horizontal movements of the eating tool within plate, i.e. the edges of the plate. Alternatively, the eating aid robot comprises sensing means detecting when the eating tool pressing against the edge of the plate and upon such detection switching to another horizontal movement within the plate.

At a point in time during this on-going horizontal movement of the eating tool in the first vertical level, i.e. moving the eating tool on and within the plate, the eating aid robot receives 110 the signal from the manoeuvre device. The eating aid robot then selects 121 the subsequent movement and/or pause of the cycle. In this example the subsequent movement and/or pause of the cycle is (a) moving the eating tool towards an edge of the plate based on the calibration of the eating aid robot with the shape of the plate or the sensing means detecting the eating tool pressing against the edge of the plate, (b) scooping with the eating tool, (c) moving the eating tool to the second vertical level and (d) pausing the arm with the eating tool in the second vertical level. Thus the eating aid robot selects (121) the subsequent movement and/or pause of the cycle, i.e. (a)-(d). Since (d) is pausing the arm with the eating tool in the second vertical level, once this "step" of the subsequent movement and/or pause of the cycle has been reached, the eating aid robot will pause the arm with the eating tool in the second vertical level until receiving 110 the signal anew from the manoeuvre device.

The on-going horizontal movement of the eating tool in the first vertical level, i.e. moving the eating tool on and within the plate may be done according to a random or a predetermined pattern as explained above. The different predetermined patterns will be described in more detail below. At a point in time, the person using the eating aid robot (i.e. the user) presses the button so that the manoeuvre device generates the signal. The user may e.g. press the button when he/she sees that the eating tool is in a position of the plate where there is a piece of food that the user wishes to consume in the next bite. Thus the user presses the button to send the signal to the eating aid robot.

When the signal is received 110, the eating aid robot will then move the arm to (a) move the eating tool towards an edge of the plate based on the calibration of the eating aid robot with the shape of the plate or the sensing means detecting the eating tool pressing against the edge of the plate. How the eating tool is moved in relation to the piece of food in order to get the piece of food with the eating tool will be described in more detail below.

Assume for example that the eating tool is a spoon, then when the spoon is moved towards the edge of the plate, the spoon may push the piece of food towards the edge of the plate. The arm then performs a (b) scooping movement with the eating tool, i.e. the spoon, in order to get the food onto the spoon. Thereafter, the arm moves (c) the eating tool to the second vertical level. The second vertical level is about the vertical height of the mouth of the user of the eating aid robot. The eating aid robot then pauses (d) the arm with the eating tool in the second vertical level. The user may then lean forward a little to take the food on the spoon with his/her mouth. In this manner, the user of the eating aid robot is enabled to control the eating aid robot with a manoeuvre device having for example just one button in order to eat by himself/herself.

Figure 1C:
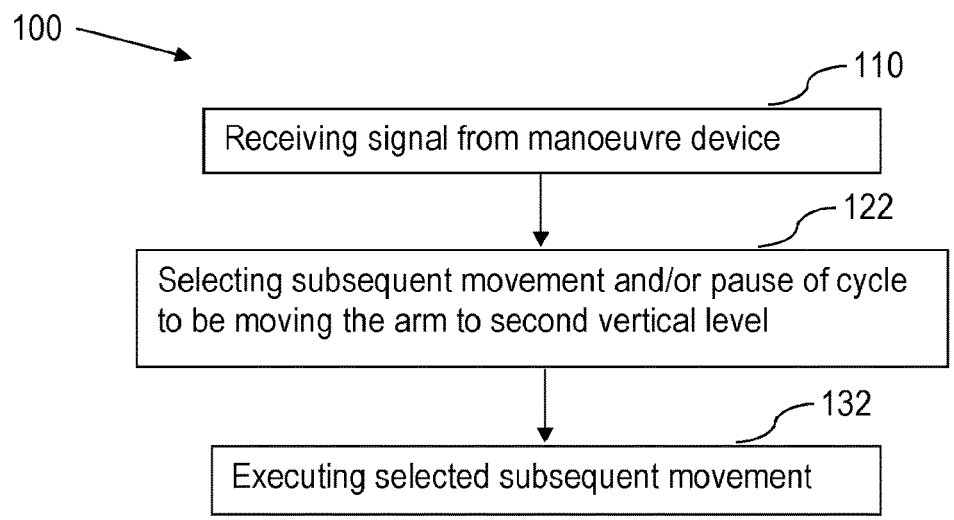
FIG. 1c is a flowchart of a method for controlling an eating aid robot according to yet an exemplifying embodiment.
Figure 1D:
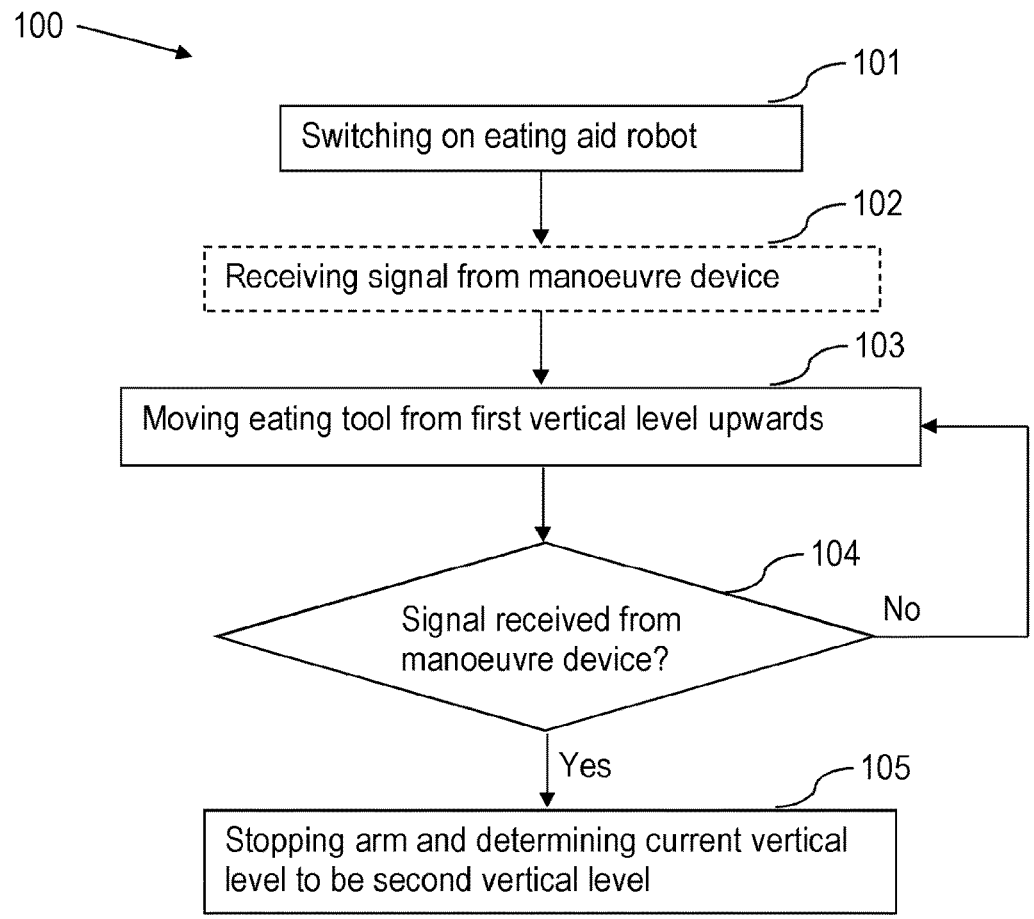
FIG. 1d is a flowchart of a method for controlling an eating aid robot according to an exemplifying embodiment.

The method may further comprise receiving 110 the signal from the manoeuvre device when the arm is currently pausing with the eating tool in the second vertical level, selecting 122 and executing 132 the subsequent movement and/or pause of the cycle for the arm to be moving the eating tool to the first vertical level, see FIG. 1c.

Either following, or independently of the example above, assume the arm is currently (d) pausing with the eating tool in the second vertical level. At a point in time, the user decides to take another bite or that he/she doesn't want to have the eating tool, e.g. the spoon, in front of his/her face. The user presses the button to send the signal to the eating aid robot. The eating aid robot receives 110 the signal and selects the subsequent movement and/or pause of the cycle. In this example the subsequent movement and/or pause of the cycle is (e) moving the eating tool to the first vertical level. The eating aid robot hence selects the (122) the subsequent movement and/or pause of the cycle, i.e. (e) moving the eating tool to the first vertical level. Then the eating aid robot executes 132 the selected movement and moves (e) the eating tool to the first vertical level, i.e. moving the eating tool to the vertical level of the plate.

Merely as an example, the subsequent movement and/or pause of the cycle following (e) may further comprise (f) pausing the eating tool at the first vertical level until the signal is received anew, or (g) horizontally moving the eating tool in the first vertical level, i.e. moving the eating tool on and within the plate, until the signal is received anew by the eating aid robot. In other words, when the arm is currently pausing (d) with the eating tool in the second vertical level, and when the signal is received 110, the subsequent movement and/or pause may be either (e)+(f) or (e)+(g).

The arm of the eating aid robot may further be capable of tilting the eating tool, wherein the method further comprises, when the eating tool is in the first vertical level corresponding to the vertical level of the plate and moving horizontally within the plate, tilting the eating tool in relation to the horizontal movement of the eating tool within the plate.

Assume for example that the eating tool is a spoon, then the spoon has a concave surface and a convex surface. The concave surface forms a recess in which food may be kept or hold. Thus when the spoon is moved horizontally, the eating aid robot tilts the spoon (see FIGS. 2c and 2d) in relation to the horizontal movement of the spoon within the plate. The tilting is such that the concave surface is tilted to be exposed to the horizontal movement of the spoon. In this manner, food being "in front of" the spoon, meaning food that hits the concave surface of the spoon, may more easily be catched or scooped onto the spoon.

The method may further comprise jiggling the eating tool after scooping and before moving the eating tool to the second vertical level and pausing the eating tool in the second vertical level until receiving 110 the signal anew from the manoeuvre device.

Figure 2A:
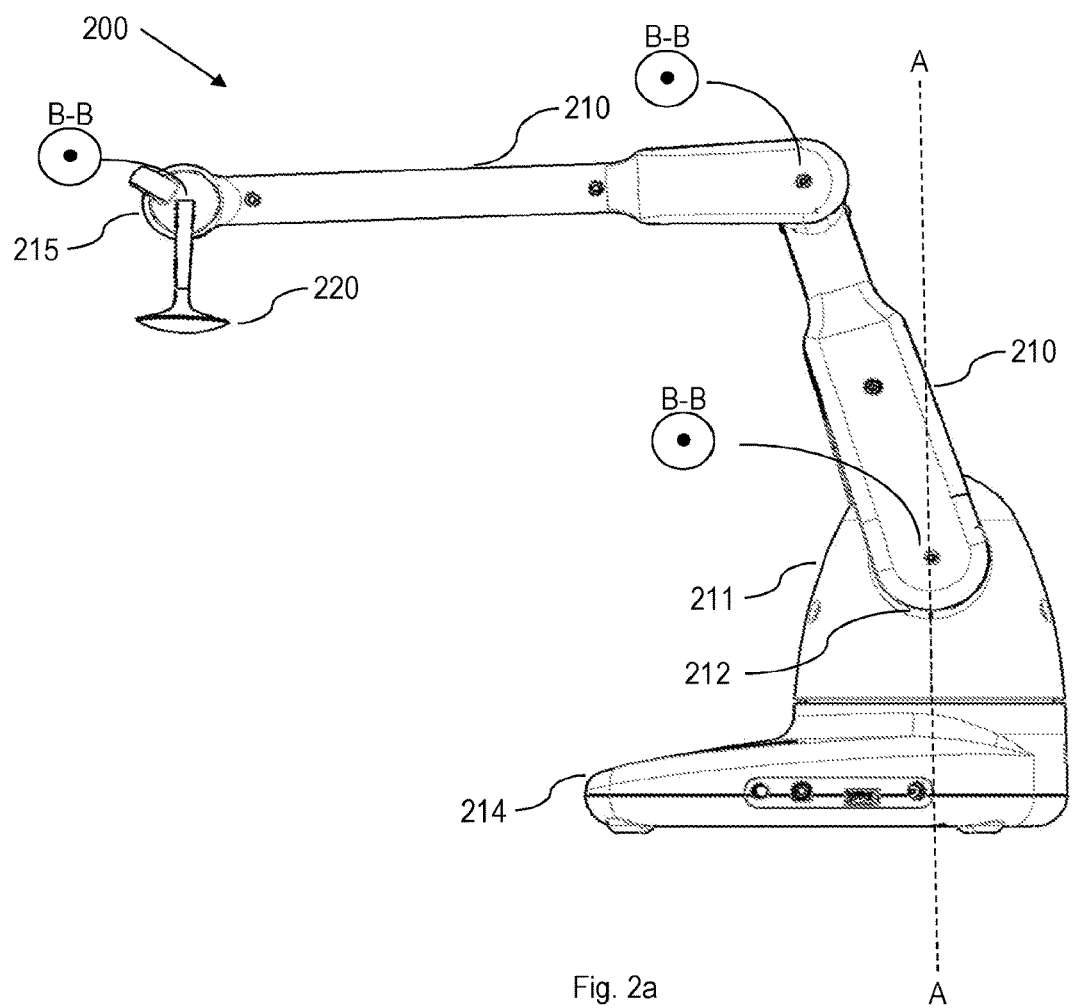
FIG. 2a is an illustration of an eating aid robot according to an exemplifying embodiment.
Figure 2B:
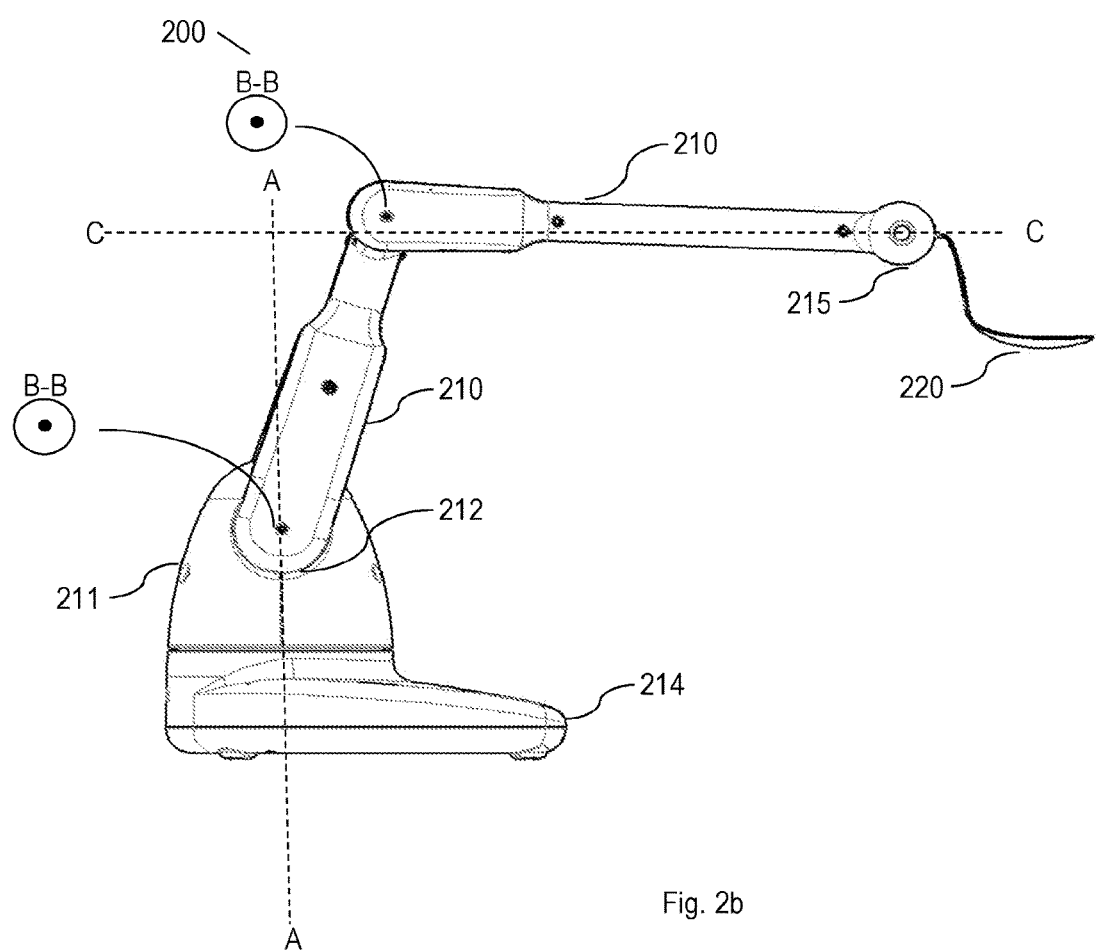
FIG. 2b is an illustration of an eating aid robot according to another exemplifying embodiment.
Figure 2C:
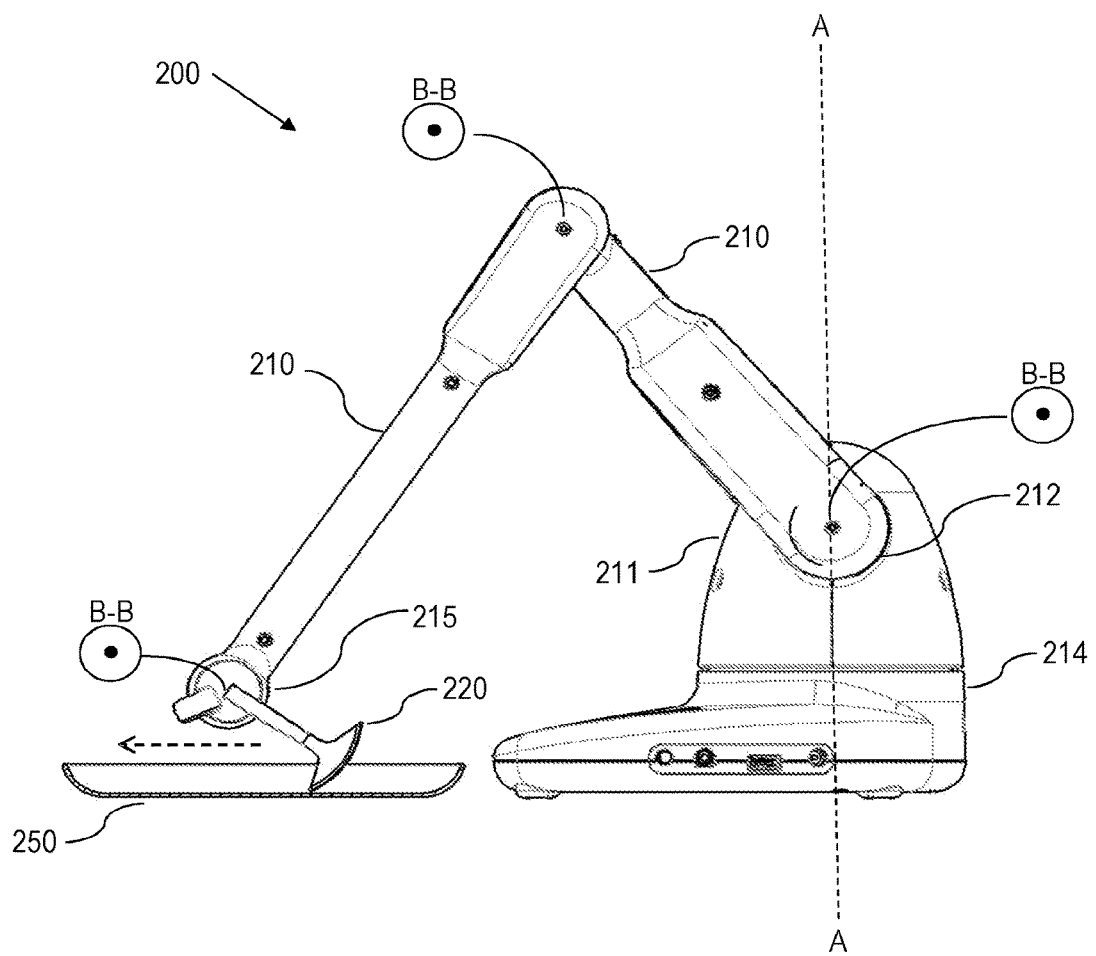
FIG. 2c is an illustration of an eating aid robot according to yet an exemplifying embodiment.

The scooping may comprise, e.g. if the eating tool is a spoon, moving the spoon from a tilted position to an "upright" or non-tilted position (see e.g. FIGS. 2a, 2b and 2c and disregard the vertical differences in the figures). In this example, the method further comprises jiggling the spoon, or eating tool, which may comprise tilting the spoon back and forth. In case a piece of food is located on the edge of the spoon, then the piece of food may fall off the spoon when moving the spoon from the first vertical level to the second vertical level. Thus, by jiggling the spoon any such piece of food at the edge of the spoon may either be moved closer to the centre of the spoon or may fall off already at the first vertical level. Thus, any piece of food falling off during moving the spoon from the first vertical level to the second vertical level and possibly landing in gravy or sauce on the plate or outside the place may be avoided. Consequently, after scooping with e.g. the spoon, the method comprises jiggling the spoon and then moving the spoon to the second vertical level and then pausing the eating tool in the second vertical level until receiving 110 the signal anew from the manoeuvre device.

The method may further comprise, when the eating aid robot is switched on 101, moving 103 the eating tool from the first vertical level upwards vertically until receiving 104 the signal from the manoeuvre device, determining 105 the second vertical level being the vertical level when the signal was received.

The eating aid robot may be powered electrically by e.g. batteries or by being connected to an electric power outlet. In order to conserve energy, the eating aid robot may be switched off when not in use. Thus, when a person wishes to use the eating aid robot, he/she may e.g. first switch on 101 the power of the eating aid robot. As described above, there may be a plurality of different options for a user to enter to the eating aid robot, e.g. the kind of food that is to be eaten, the type of plate to be used, which eating tool is engaged at the end of the arm and so on. At one point in time, the arm of the eating aid robot may start moving the arm to move the eating tool from the first vertical position corresponding to the plate upwards vertically. The eating aid robot continues to move 103 the arm to move the eating tool vertically upwards until the eating aid robot receives 104 the signal from the manoeuvre device. At the moment the eating aid robot receives the 104 the signal, the vertical upwards movement of the eating tool stops 105 and the eating aid robot determines the second vertical level to be the vertical level when the signal was received. Thus a user sitting at a table next to the eating aid robot may easily configure the eating aid robot to his/her own preferences and circumstances. Hence, when the user thinks the eating tool is in a good position for him/her to take food from the eating tool, the user simply presses e.g. a button on the manoeuvre device and the second vertical level is determined.

The method may also comprise initiating the vertical upwards movement of the eating tool by e.g. pressing a button on the manoeuvre device to send a signal to the eating aid robot to start the upwards movement of the eating tool from the first vertical position at the plate.

FIGS. 2a-2d are illustrations of an eating aid robot according to exemplifying embodiments.

FIGS. 2a-2d illustrate the eating aid robot 200 comprising an arm 210 which in turn may comprise individual elements joined together so that they may move in relation to each other. The joint of the two elements of the arm are indicated to enable the elements to be movable in relation to each other by being turnable around an axis B-B which is perpendicular to the plane of the drawing. An end 212 of the arm 210, i.e. an end 212 of one of the elements of the arm 210, is connected to a first base element 211 by means of a turnable joint turnable around an axis B-B which is perpendicular to the plane of the drawing. The base element 211 is in turn turnably connected to a second base element 214 such that the first base element 211 is turnable around and axis A-A.

FIGS. 2a-2d further illustrate an end 215 of the arm, i.e. an end 215 of one of the elements of the arm 210, is capable of engaging an eating tool 220 at the end 215 of the arm. The eating tool 220 is further turnably engaged at the end of the arm so that the eating tool may be rotated around an axis B-B which is perpendicular to the plane of the drawing.

Figure 2D:
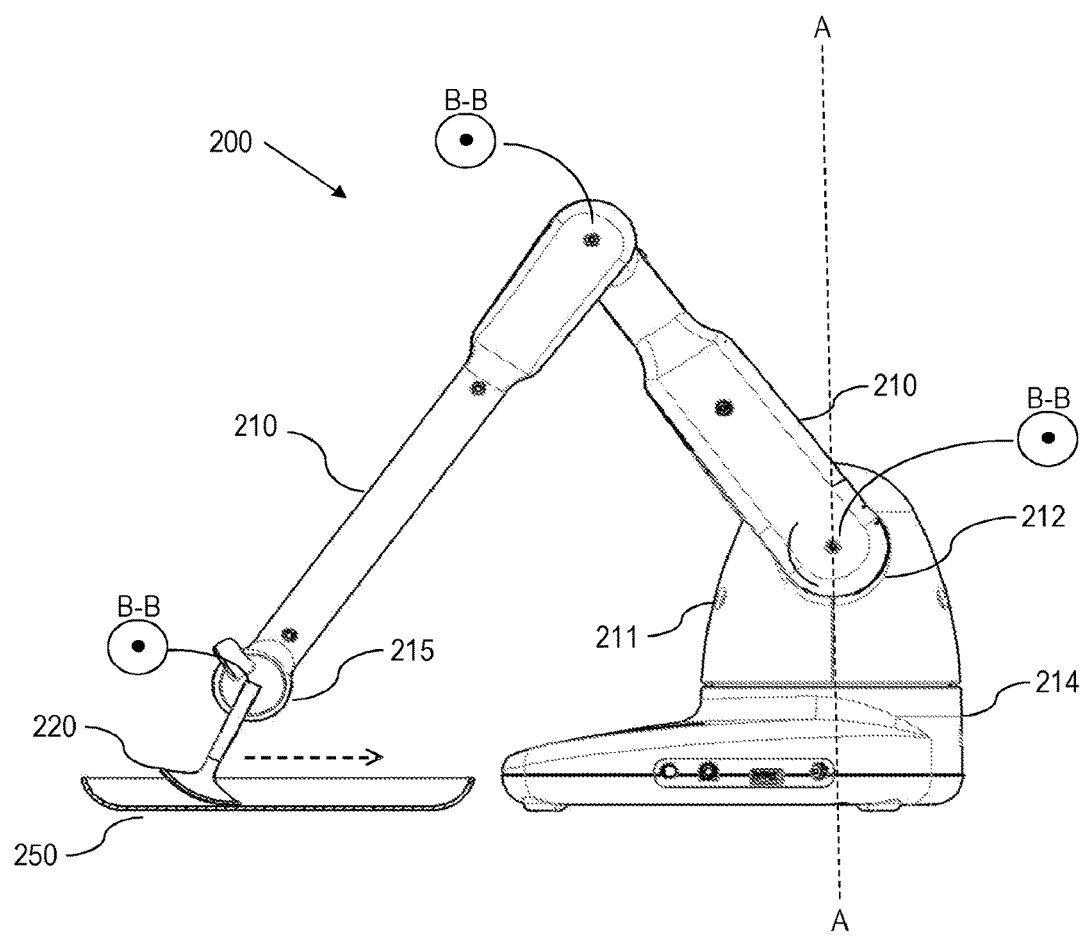
FIG. 2d is an illustration of an eating aid robot according to still an exemplifying embodiment.

FIGS. 2c and 2d illustrate one exemplifying vertical level of the eating tool 220 corresponding to the vertical level of a plate 250. FIGS. 2a and 2b illustrate another exemplifying vertical level of the eating tool 220 to be at a height above the vertical level of a plate 250, even though the plate is not shown in FIGS. 2a and 2b. The vertical level illustrated in FIGS. 2a and 2b may correspond to a vertical level suitable for a user of the eating aid robot to take the food from the eating tool. In FIG. 2b, the eating tool is turnable, or tiltable, around and axis C-C illustrated by a dotted line.

FIGS. 2c and 2d further illustrate the eating aid robot 200 tilting the eating tool 220 (e.g. a spoon) in relation to the horizontal movement of the eating tool 220 within the plate 250. For example, in FIG. 2c the eating aid robot 230 is moving the arm 210 to move the eating tool 220 in a direction away from the first and the second base elements 211 and 214. The eating aid robot 200 thus tilts the eating tool 220 so that the concave surface of the eating tool (spoon in the illustrated example) faces the direction of the horizontal movement. Likewise, in FIG. 2d, the eating aid robot 230 is moving the arm 210 to move the eating tool 220 in a direction towards the first and the second base elements 211 and 214. The eating aid robot 200 thus tilts the eating tool 220 so that the concave surface of the eating tool (spoon in the illustrated example) faces the direction of the horizontal movement.

The cycle of different vertical and horizontal movements and pauses when the arm 210 is kept still with the eating tool 220 in at least one of the vertical levels may comprise a plurality of different horizontal movements of the eating tool 220 within the plate 250.

In an example, as described above, the cycle comprises a plurality of different movements and/or pauses (a) move the eating tool towards an edge of the plate, (b) scooping movement with the eating tool, (c) moving the eating tool to the second vertical level, (d) pausing the arm with the eating tool in the second vertical level, (e) moving the eating tool to the first vertical level, (f) pausing the eating tool at the first vertical level until the signal and (g) horizontally moving the eating tool in the first vertical level, i.e. moving the eating tool on and within the plate. The reception of the signal may trigger a single movement and/or pause; or trigger a plurality of different individual movements and/or a pause.

In another example, the eating aid robot may start for example with (d). When the eating aid robot receives the signal, it performs (e)→(g) during e.g. 5 seconds, then goes to (a)+(b)+(c)+(d) and pauses the arm for e.g. 10 seconds the starts over with (e)→(g) and so on. The eating aid robot continuously performs these different movements and pauses until it receives the signal wherein the eating aid robot e.g. (c) moves the eating tool to the second vertical level and pauses it there until the signal is received anew. In this manner, the user need not use the manoeuvre device other than when the user wishes to start, pause and/or finish the eating. This may be desirable when the user find it difficult even to press to button too many times.

In the other examples described earlier, the eating aid robot pauses the arm with the eating tool kept still until the signal is received anew. The difference between these examples is the configuration of the cycle. Thus, the cycle may comprise a plurality of different individual movements and/or pauses separated by the need for the reception of the signal, or the cycle may comprise a plurality of different movements and/or pauses in one chunk or flow which is repeated until the signal is received.

As also described above, the arm 210 may move the eating tool 220 horizontally within the plate 250 when the eating tool 220 is in the first vertical level. The horizontal movement within the plate may either be performed according to a predetermined or a random pattern. An example of a predetermined pattern is illustrated in FIG. 2e.

Figure 2E:
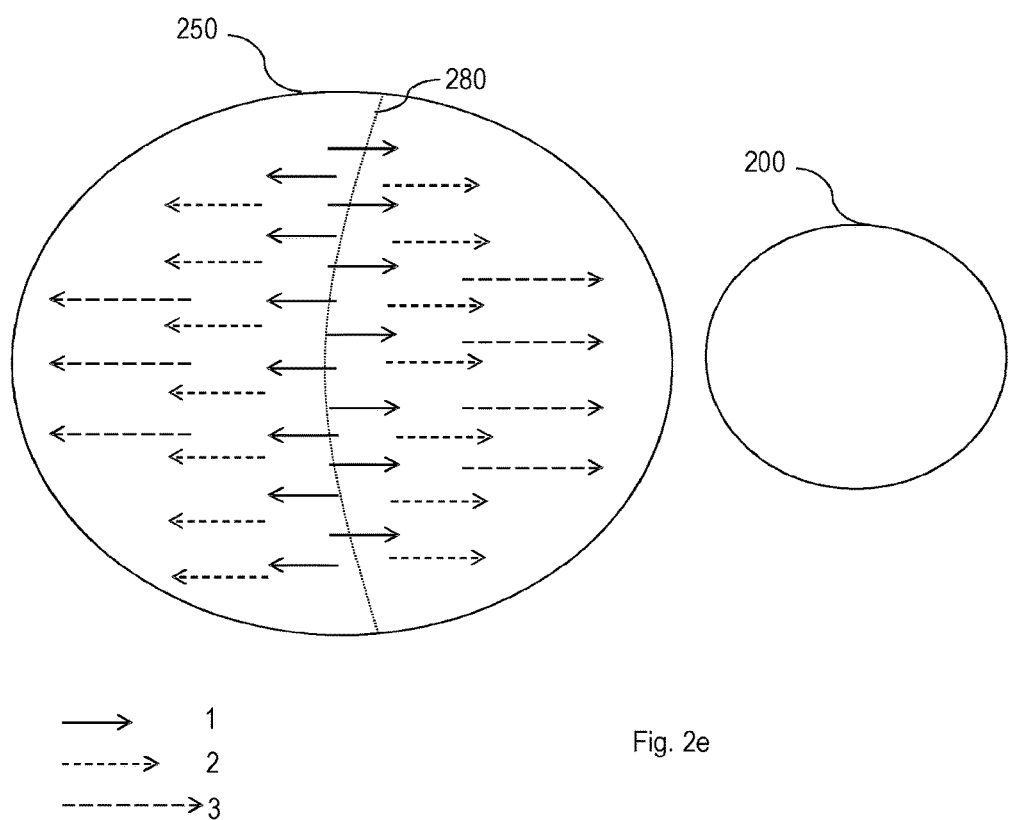
FIG. 2e is an illustration of an exemplifying horizontal moving pattern of an eating tool of an eating aid robot within a plate.

FIG. 2e schematically illustrates the eating aid robot 200 and a plate 250. As described with reference to FIGS. 2a-2d, the arm 210 of the eating aid robot is connected to a first base element 211 by means of a turnable joint, turnable around an axis B-B which is perpendicular to the plane of the drawing. The base element 211 is in turn turnably connected to a second base element 214 such that the first base element 211 is turnable around and axis A-A. In FIG. 2e, the axis A-A is perpendicular to the figure. Thus when the first base element 211 turns around the axis A-A, keeping the eating tool as a constant distance from the base element, the eating tool may be moved along the dotted line 280 of FIG. 2e.

In an example, the eating aid robot moves the arm to move the eating tool first along the non-dotted arrows marked as 1 in the figure. The first time the eating aid robot starts with the uppermost arrow pointing to the right. The eating aid robot moves the eating tool (upon reception of the signal) to the base of one of the non-dotted arrows marked as 1, e.g. the uppermost arrow and moves the eating tool from the left to the right, from the base to the tip of the arrow, and scoops and then moves to the second vertical level enabling a user of the eating aid robot to take the food from the eating tool. When the eating aid robot receives the signal anew, the eating aid robot moves the arm to move the eating tool to base of the next non-dotted arrow, e.g. the one below the uppermost arrow and moves the eating tool from the right to the left, from the base to the tip of the arrow, and scoops and then moves to the second vertical level enabling a user of the eating aid robot to take the food from the eating tool. The order in which of the arrows are followed by the eating tool may be predetermined or random. Thereafter, when receiving the signal anew, the eating aid robot moves to the next non-dotted arrow until it has moved the eating tool from the base to the tip of the lowermost arrow of FIG. 2e. When in the second vertical position and receiving the signal, the eating aid robot moves the arm to move the eating tool to e.g. the uppermost dotted arrow denoted 2 and pointing from left to right. The eating aid robot then follows the pattern of all the dotted arrows denoted 2 in the same manner as described for the non-dotted arrows. Thereafter, the eating aid robot starts with e.g. the uppermost dotted arrow denoted 3 and follows the same procedure as described for the non-dotted arrows. It shall be pointed out that this is merely an example of a predetermined pattern and there may be a vast amount of different predetermined or random pattern, which may also be dependent on the type of food to be eaten and on the eating tool used.

In another example, when the eating aid robot is moving the eating tool horizontally in the first vertical level, the eating aid robot moves the eating tool along the dotted line 280 back and forth until receiving the signal from the manoeuvre device. When receiving the signal, the eating aid robot changes from moving the eating tool along the dotted line 280 and directly starts moving the eating tool either to the left or to the right in FIG. 2e towards an edge of the plate 250, scoops and moves the eating tool to the second vertical level and pauses the arm with the eating tool in the second vertical level until receiving the signal anew. When the signal is received, the eating aid robot again moves the eating tool to the first vertical position and starts moving the eating tool along the dotted line 280 until receiving the signal anew. If the eating aid robot previously moved the eating tool from e.g. the dotted line 280 to the right, the eating aid robot moves the eating tool from the dotted line 280 to the left towards an edge of the plate 250, scoops and moves the eating tool to the second vertical level and pauses the arm with the eating tool in the second vertical level until receiving the signal anew. Alternatively, the eating aid robot may further tilt the eating tool, when the eating tool is a spoon, with the concave side facing the eating robot if the eating aid robot will move the spoon to the right in the FIG. 2e when receiving the signal during moving the eating tool along the dotted line 280. Likewise, the eating aid robot may further tilt the eating tool, when the eating tool is a spoon, with the convex side facing the eating robot if the eating aid robot will move the spoon to the left in the FIG. 2e when receiving the signal during moving the eating tool along the dotted line 280.

In still an example, not illustrated in the figures, the plate 250 is e.g. a bento box or is having different pieces of food places at different places of the plate 250. Further in this example, the eating tool may be a gripping tool. The eating aid robot may be holding the eating tool in the second vertical level in order for a user to take the food with his/her mouth from the eating tool. The user gives the signal via the manoeuvre device and the eating aid robot moves the eating tool to a first vertical level which in this example is just above the plate and starts moving the eating tool horizontally in the first vertical level, wherein the horizontal movements correspond to the different places of the plate 250 where different pieces of food may be placed. When the eating aid robot receives the signal, the eating aid robot moves the eating tool (the gripping tool) vertically downwards to the level of the plate, performs a gripping action with the gripping tool and moves the gripping tool to the second vertical level in order for a user to take the food in his/her mouth form the eating tool.

Embodiments herein also relate to an eating aid robot. The eating aid robot has the same objects, technical features and advantages as the method performed by the eating aid robot. The eating aid robot will only be described in brief in order to avoid unnecessary repetition. Exemplifying embodiments of the eating aid robot will now briefly be described with reference to FIG. 3 in conjunction with FIGS. 2a-2d.

Figure 3:
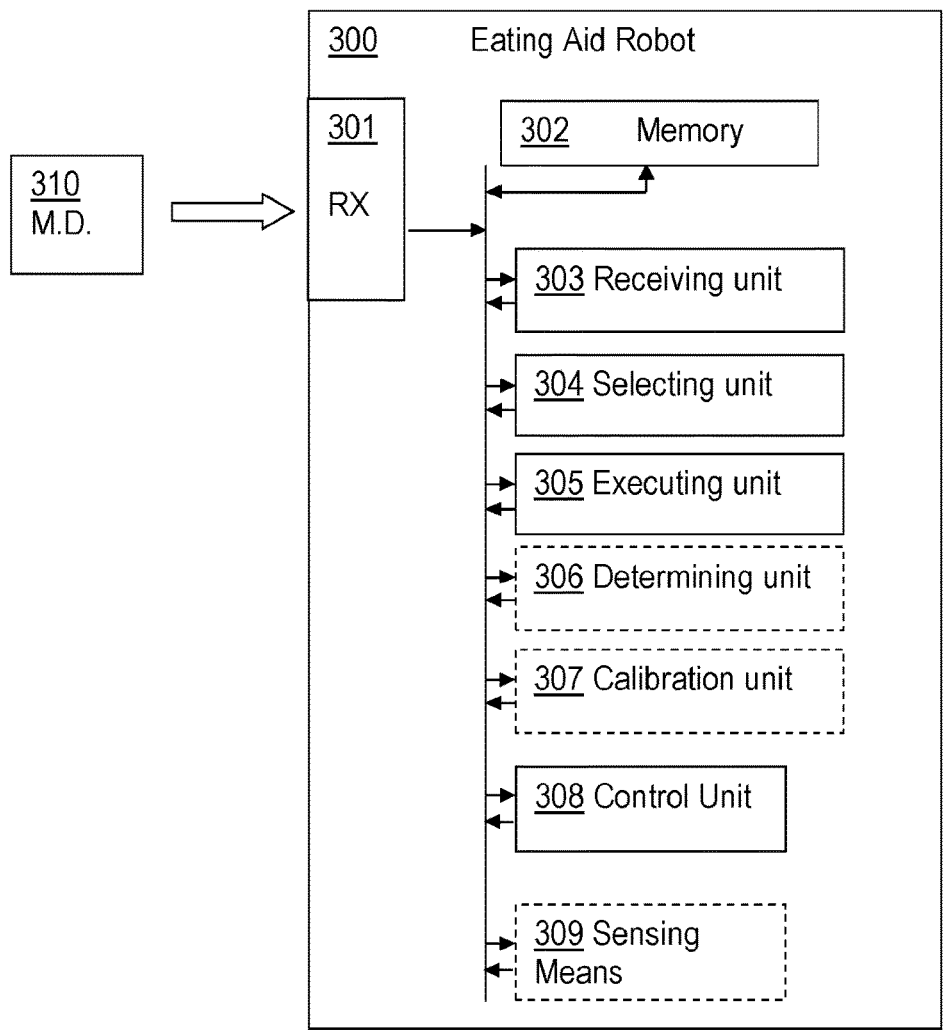
FIG. 3 is a block diagram of an eating aid robot according to an exemplifying embodiment.

The eating aid robot 200, 300 comprises an arm 210 capable of engaging an eating tool 220 at an end 215 of the arm, the arm 210 being moveable to move the eating tool 220 horizontally and vertically, wherein the arm 210 of the eating aid robot 200, 300 is configured to be positioned with the eating tool 220 in at least two vertical levels, a first vertical level and a second vertical level at a vertical height above the first vertical level. The eating aid robot 200, 300 is connectable to a manoeuvre device 310 which sends a signal to the eating aid robot 200, 300 at various time instances during operation of the eating aid robot 200, 300, wherein the arm 210 of the eating robot further follows a cycle of different vertical and horizontal movements and pauses when the arm 210 is kept still with the eating tool 220 in at least one of the vertical levels. FIG. 3 illustrates the eating aid robot 200, 300 comprising a receiving unit 303 adapted for receiving the signal from the manoeuvre device 310; and a selecting unit 304 adapted for selecting a subsequent movement and/or pause of the cycle for the arm 210 based on in which of the movements or pauses of the cycle the arm 210 currently is when receiving the signal. The eating aid robot 200, 300 further comprises an executing unit 305 adapted for executing the selected subsequent movement and/or pause of the cycle until a, or the, signal is received anew from the manoeuvre device.

It shall be pointed out that FIG. 3 also illustrate the eating aid robot comprising further units, which are dotted in the figure. These other dotted units are optional and are therefore illustrated in the figure by the dotted lines.

The eating aid robot may have the same advantages as the method performed by the eating aid robot. For a person who may have difficulty manoeuvring e.g. a joystick in different directions, or pressing a plurality of different buttons, in order to control the arm and thus the eating tool, a simple button is enough to control the movements of the arm and thus the eating tool, or pressing any button out of a plurality of buttons, moving a joystick in any of a plurality of directions is enough to control the movements of the arm and thus the eating tool. A person having difficulties eating himself/herself may experience enhanced eating quality by an easily controllable eating aid robot.

According to an embodiment, the eating aid robot is calibrated to a plate 250 with regard to a vertical level of the plate 250, or wherein the eating aid robot comprises sensing means 309 adapted to detect when the eating tool 220 is pressing against a surface of the plate 250, wherein the first vertical level corresponds to the vertical level of the plate 250.

According to still an embodiment, the eating aid robot further is calibrated to a plate 250 with regard to the shape of the plate 250, or comprises sensing means 309 adapted to detect when the eating tool 220 is pressing against an edge of the plate 250, the eating aid robot 200, 300 is adapted to, when the arm is positioned with the eating tool in the first vertical level corresponding to a vertical level of the plate 250, move the arm 210 to move the eating tool 220 horizontally within the plate 250 according to a random pattern.

According to another embodiment, the eating aid robot further is calibrated to a plate 250 with regard to the shape of the plate 250, or comprises sensing means 309 adapted to detect when the eating tool 220 is pressing against an edge of the plate 250, the eating aid robot 200, 300 is adapted to, when the arm is positioned with the eating tool in the first vertical level corresponding to a vertical level of the plate 250, move the arm 210 to move the eating tool 220 horizontally within the plate 250 according to a predetermined pattern.

According to yet an embodiment, the receiving unit 303 further is adapted for receiving the signal from the manoeuvre device 310 when the arm 210 is currently holding the eating tool 220 in the first vertical level and moving the arm 210 to move the eating tool 220 within the plate, wherein the selecting unit 304 and the executing unit 305 respectively are adapted for selecting and executing the subsequent movement and/or pause of the cycle for the arm 210 to be moving the eating tool 220 towards an edge of the plate 250 based on the calibration of the eating aid robot 200, 300 with the shape of the plate or the sensing means 309 detecting the eating tool 220 pressing against the edge of the plate 250, scooping with the eating tool 220, moving the eating tool 220 to the second vertical level and pausing the arm 210 with the eating tool 220 in the second vertical level until the receiving unit 303 receives the signal anew from the manoeuvre device 310.

According to an embodiment, the receiving unit 303 further is adapted for the signal from the manoeuvre device 310 when the arm 210 is currently pausing with the eating tool 220 in the second vertical level, wherein the selecting unit 304 and the executing unit 305 respectively are adapted for selecting and executing the subsequent movement and/or pause of the cycle for the arm 210 to be moving the eating tool 220 to the first vertical level.

According to still an embodiment, the arm 210 is adapted for tilting the eating tool 220, the eating aid robot 200, 300 further being adapted for, when the eating tool 220 is in the first vertical level corresponding to the vertical level of the plate 250 and moving horizontally within the plate 250, tilting the eating tool 220 in relation to the horizontal movement of the eating tool 220 within the plate 250.

According to yet an embodiment, the arm 210 is adapted for jiggling the eating tool 220 after scooping and before moving the eating tool to the second vertical level and pausing the eating tool in the second vertical level until the receiving unit 303 receives the signal anew from the manoeuvre device 310.

According to yet an embodiment, the executing unit 305 further is adapted for, when the eating aid robot 200, 300 is switched on, moving the eating tool 220 from the first vertical level upwards vertically until the receiving unit 303 receives the signal from the manoeuvre device 310, the eating aid robot 200, 300 further comprising a determining unit 306 adapted for determining the second vertical level being the vertical level when the signal was received by the receiving unit 303.

In FIG. 3, the eating aid robot 300 is also illustrated comprising a receiving interface 301. Through this interface, the eating aid robot 300 is adapted to communicate with the manoeuvre device. The receiving interface 301 may comprise more than one receiving arrangement. For example, the receiving interface may be connected to both a wire and an antenna, by means of which the eating aid robot 300 is enabled to communicate with the manoeuvre device. The eating aid robot 300 further comprises a memory 302 for storing data. Further, the eating aid robot 300 is illustrated comprising a control or processing unit 308 which in turns is connected to the different units 303-307. It shall be pointed out that this is merely an illustrative example and the eating aid robot 300 may comprise more, less or other units or modules which execute the functions of the eating aid robot 300 in the same manner as the units illustrated in FIG. 3.

It should be noted that FIG. 3 merely illustrates various functional units in the eating aid robot 300 in a logical sense. The functions in practice may be implemented using any suitable software and hardware means/circuits etc. Thus, the embodiments are generally not limited to the shown structures of the eating aid robot 300 and the functional units. Hence, the previously described exemplary embodiments may be realised in many ways. For example, one embodiment includes a computer-readable medium having instructions stored thereon that are executable by the control or processing unit 308 for executing the method steps in the eating aid robot 300. The instructions executable by the computing system and stored on the computer-readable medium perform the method steps of the eating aid robot 300 as set forth in the claims.

Figure 4:
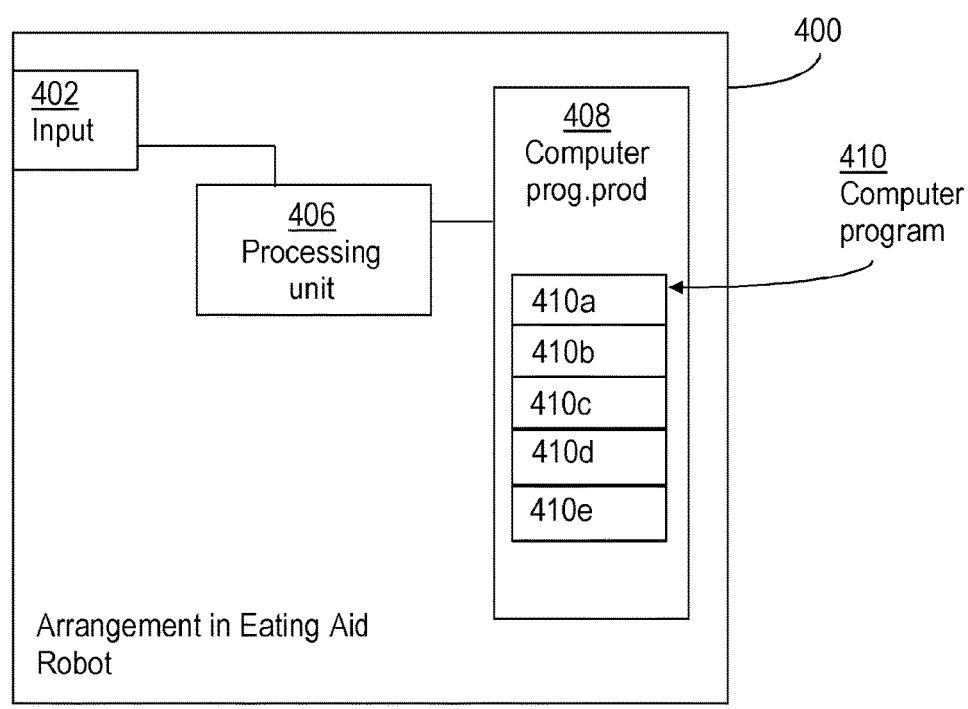
FIG. 4 is a block diagram of an arrangement in an eating aid robot according to an exemplifying embodiment.

FIG. 4 schematically shows an embodiment of an arrangement in an eating aid robot 400. Comprised in the eating aid robot 400 are here a processing unit 406, e.g. with a DSP (Digital Signal Processor). The processing unit 406 may be a single unit or a plurality of units to perform different actions of procedures described herein. The eating aid robot 400 may also comprise an input unit 402 for receiving signals from other entities, and an output unit 404 for providing signal(s) to other entities. The input unit and the output unit may be arranged as an integrated entity or as illustrated in the example of FIG. 3, as one or more interfaces 301.

Furthermore, the eating aid robot 400 comprises at least one computer program product 408 in the form of a non-volatile memory, e.g. an EEPROM (Electrically Erasable Programmable Read-Only Memory), a flash memory and a hard drive. The computer program product 408 comprises a computer program 410, which comprises code means, which when executed in the processing unit 406 in the eating aid robot 400 causes the eating aid robot 400 to perform the actions e.g. of the procedure described earlier in conjunction with FIGS. 1a-1d.

The computer program 410 may be configured as a computer program code structured in computer program modules 410a-410e. Hence, in an exemplifying embodiment, the code means in the computer program of the eating aid robot 400 comprises a receiving unit, or module, for receiving the signal from the manoeuvre device. The computer program further comprises a selecting unit, or module, for selecting a subsequent movement and/or pause of the cycle for the arm based on in which of the movements or pauses of the cycle the arm currently is when receiving the signal. The computer program further comprises an executing unit, or module, for executing the selected subsequent movement and/or pause of the cycle until the signal is received anew from the manoeuvre device.

The computer program modules could essentially perform the actions of the flow illustrated in FIGS. 1a-1d, to emulate the eating aid robot 400. In other words, when the different computer program modules are executed in the processing unit 406, they may correspond to the units 303-307 of FIG. 3.

Although the code means in the respective embodiments disclosed above in conjunction with FIG. 3 are implemented as computer program modules which when executed in the respective processing unit causes the eating aid robot to perform the actions described above in the conjunction with figures mentioned above, at least one of the code means may in alternative embodiments be implemented at least partly as hardware circuits.

The processor may be a single CPU (Central processing unit), but could also comprise two or more processing units. For example, the processor may include general purpose microprocessors; instruction set processors and/or related chips sets and/or special purpose microprocessors such as ASICs (Application Specific Integrated Circuit). The processor may also comprise board memory for caching purposes. The computer program may be carried by a computer program product connected to the processor. The computer program product may comprise a computer readable medium on which the computer program is stored. For example, the computer program product may be a flash memory, a RAM (Random-access memory) ROM (Read-Only Memory) or an EEPROM, and the computer program modules described above could in alternative embodiments be distributed on different computer program products in the form of memories within the eating aid robot.

It is to be understood that the choice of interacting units, as well as the naming of the units within this disclosure are only for exemplifying purpose, and nodes suitable to execute the method described above may be configured in a plurality of alternative ways in order to be able to execute the suggested procedure actions.

It should also be noted that the units described in this disclosure are to be regarded as logical entities and not with necessity as separate physical entities.

While the embodiments have been described in terms of several embodiments, it is contemplated that alternatives, modifications, permutations and equivalents thereof will become apparent upon reading of the specifications and study of the drawings. It is therefore intended that the following appended claims include such alternatives, modifications, permutations and equivalents as fall within the scope of the embodiments and defined by the pending claims.

The invention claimed is:

1. A method for controlling an eating aid robot comprising an arm capable of engaging an eating tool at an end of the arm, the method comprising:
   receiving a signal from a maneuver device adapted to be connected to the eating aid robot and to send a signal to the robot upon actuation of the maneuver device during an operation of the eating aid robot,
   selecting a subsequent vertical or horizontal movement and/or pause, wherein the arm is maintained with the eating tool in one of at least two vertical levels, of a pre-defined cycle for the arm, based on in which of the movements or pauses of the pre-defined cycle the arm currently is when receiving the signal, and
   executing the selected subsequent vertical or horizontal movement and/or pause of the pre-defined cycle until a signal is received anew from the maneuver device,
   wherein the steps of selecting and executing a subsequent movement and/or pause of the pre-defined cycle are performed irrespective of the type of signal received from the maneuver device.

2. A method according to claim 1, wherein the eating aid robot further is calibrated to a plate with regard to the shape of the plate, or comprises sensing means adapted to detect when the eating tool is pressing against an edge of the plate, the method comprising, when the arm is positioned with the eating tool in the first vertical level corresponding to a vertical level of the plate, moving the arm to move the eating tool horizontally within the plate according to a random pattern.

3. A method according to claim 1, wherein the eating aid robot further is calibrated to a plate with regard to the shape of the plate, or comprises sensing means adapted to detect when the eating tool is pressing against an edge of the plate, the method comprising, when the arm is positioned with the eating tool in the first vertical level corresponding to a vertical level of the plate, moving the arm to move the eating tool horizontally within the plate according to a predetermined pattern.

4. A method according to claim 2, the method further comprising receiving the signal from the maneuver device when the arm is currently holding the eating tool in the first vertical level and moving the eating tool within the plate, selecting and executing the subsequent movement and/or pause of the pre-defined cycle for the arm to be moving the eating tool towards an edge of the plate based on the calibration of the eating aid robot with the shape of the plate or the sensing means detecting the eating tool pressing against the edge of the plate, scooping with the eating tool, moving the eating tool to the second vertical level and pausing the arm with the eating tool in the second vertical level until receiving the signal anew from the maneuver device.

5. A method according to claim 1, the method further comprising receiving the signal from the maneuver device when the arm is currently pausing with the eating tool in the second vertical level, selecting and executing the subsequent movement and/or pause of the pre-defined cycle for the arm to be moving the eating tool to the first vertical level.

6. A method according to claim 1, wherein the arm is capable of tilting the eating tool, the method further comprising, when the eating tool is in the first vertical level corresponding to the vertical level of the plate and moving horizontally within the plate, tilting the eating tool in relation to the horizontal movement of the eating tool within the plate.

7. A method according to claim 4, further comprising jiggling the eating tool after scooping and before moving the eating tool to the second vertical level and pausing the eating tool in the second vertical level until receiving the signal anew from the maneuver device.

8. A method according to claim 1, further comprising, when the eating aid robot is switched on, moving the eating tool from the first vertical level upwards vertically until receiving the signal from the maneuver device, determining the second vertical level being the vertical level when the signal was received.

9. An eating aid robot comprising an arm capable of engaging an eating tool at an end of the arm, the arm being moveable to move the eating tool horizontally and vertically, wherein the arm of the eating aid robot is configured to be positioned with the eating tool in at least two vertical levels, a first vertical level and a second vertical level at a vertical height above the first vertical level, the eating aid robot being connectable to a maneuver device adapted to sends a signal to the eating aid robot upon actuation of the maneuver device during operation of the eating aid robot, wherein the arm of the eating robot further follows a pre-defined cycle of different vertical and horizontal movements and pauses, wherein the arm is maintained with the eating tool in at least one of the vertical levels, the eating aid robot comprising:
   a receiving unit adapted for receiving the signal from the maneuver device,
   a selecting unit adapted for selecting a subsequent movement and/or pause of the pre-defined cycle for the arm based on in which of the movements or pauses of the pre-defined cycle the arm currently is when receiving the signal, and
   an executing unit adapted for executing the selected subsequent movement and/or pause of the pre-defined cycle until a signal is received anew from the maneuver device
   wherein the eating aid robot is adapted to perform the selection and execution of a subsequent movement and/or pause of the pre-defined cycle irrespective of the type of signal received from the maneuver device.

10. An eating aid robot according to claim 9, wherein the eating aid robot is calibrated to a plate with regard to a vertical level of the plate, or wherein the eating aid robot comprises sensing means adapted to detect when the eating tool is pressing against a surface of the plate, wherein the first vertical level corresponds to the vertical level of the plate.

11. An eating aid robot according to claim 9, wherein the eating aid robot further is calibrated to a plate with regard to the shape of the plate, or comprises sensing means adapted to detect when the eating tool is pressing against an edge of the plate, the eating aid robot is adapted to, when the arm is positioned with the eating tool in the first vertical level corresponding to a vertical level of the plate, move the arm to move the eating tool horizontally within the plate according to a random pattern.

12. An eating aid robot according to claim 9, wherein the eating aid robot further is calibrated to a plate with regard to the shape of the plate, or comprises sensing means adapted to detect when the eating tool is pressing against an edge of the plate, the eating aid robot is adapted to, when the arm is positioned with the eating tool in the first vertical level corresponding to a vertical level of the plate, move the arm to move the eating tool horizontally within the plate according to a predetermined pattern.

13. An eating aid robot according to claim 11, wherein the receiving unit further is adapted for receiving the signal from the maneuver device when the arm is currently holding the eating tool in the first vertical level and moving the arm to move the eating tool within the plate, wherein the selecting unit and the executing unit respectively are adapted for selecting and executing the subsequent movement and/or pause of the pre-defined cycle for the arm to be moving the eating tool towards an edge of the plate based on the calibration of the eating aid robot with the shape of the plate or the sensing means detecting the eating tool pressing against the edge of the plate, scooping with the eating tool, moving the eating tool to the second vertical level and pausing the arm with the eating tool in the second vertical level until the receiving unit receives the signal anew from the maneuver device.

14. An eating aid robot according to claim 9, wherein the receiving unit further is adapted for the signal from the maneuver device when the arm is currently pausing with the eating tool in the second vertical level, wherein the selecting unit and the executing unit respectively are adapted for selecting and executing the subsequent movement and/or pause of the pre-defined cycle for the arm to be moving the eating tool to the first vertical level.

15. An eating aid robot according to claim 10, wherein the arm is adapted for tilting the eating tool, the eating aid robot further being adapted for, when the eating tool is in the first vertical level corresponding to the vertical level of the plate and moving horizontally within the plate, tilting the eating tool in relation to the horizontal movement of the eating tool within the plate.

16. An eating aid robot according to claim 15, wherein the arm is adapted for jiggling the eating tool after scooping and before moving the eating tool to the second vertical level and pausing the eating tool in the second vertical level until the receiving unit receives the signal anew from the maneuver device.

17. An eating aid robot according to claim 9, wherein the executing unit further is adapted for, when the eating aid robot is switched on, moving the eating tool from the first vertical level upwards vertically until the receiving unit receives the signal from the maneuver device, the eating aid robot further comprising a determining unit adapted for determining the second vertical level being the vertical level when the signal was received by the receiving unit.

18. A non-transitory computer-readable medium encoding instructions for a computer system comprised in an arrangement in an eating aid robot, the eating aid robot comprising an arm capable of engaging an eating tool at an end of the arm, the arm being moveable to move the eating tool horizontally and vertically, wherein the arm of the eating aid robot is configured to be positioned with the eating tool in at least two vertical levels, a first vertical level and a second vertical level at a vertical height above the first vertical level, the eating aid robot being connectable to a maneuver device adapted to sends a signal to the eating aid robot upon actuation of the maneuver device during operation of the eating aid robot, wherein the arm of the eating robot further follows a pre-defined cycle of different vertical and horizontal movements and pauses, wherein the arm is maintained with the eating tool in at least one of the vertical levels, the eating aid robot comprising:
   a receiving unit adapted for receiving the signal from the maneuver device,
   a selecting unit adapted for selecting a subsequent movement and/or pause of the pre-defined cycle for the arm based on in which of the movements or pauses of the pre-defined cycle the arm currently is when receiving the signal, and an executing unit adapted for executing the selected subsequent movement and/or pause of the pre-defined cycle until a signal is received anew from the maneuver device which instructions, when executed by the computer system comprised in the arrangement in the eating aid robot, cause the eating aid robot to perform a corresponding method for controlling the eating aid robot, the method comprising:

receiving the signal from the maneuver device, selecting a subsequent movement and/or pause of the pre-defined cycle for the arm based on in which of the movements or pauses of the pre-defined cycle the arm currently is when receiving the signal, and executing the selected subsequent movement and/or pause of the pre-defined cycle until a signal is received anew from the maneuver device wherein the steps of selecting and executing a subsequent movement and/or pause of the pre-defined cycle are performed irrespective of the type of signal received from the maneuver device.

19. A non-transitory computer-readable medium encoding instructions product comprising non-transitory computer-readable medium encoding instructions according to claim 18.

* * * * *